United States Patent
Shaw

(10) Patent No.: US 12,195,518 B2
(45) Date of Patent: *Jan. 14, 2025

(54) METHODS FOR TREATING CANCER USING SOLUBLE FORMS OF PSGL-1 AND FUSION MOLECULES THEREOF

(71) Applicant: Gray D Shaw, Plymouth, MA (US)

(72) Inventor: Gray D Shaw, Plymouth, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/091,361

(22) Filed: Dec. 29, 2022

(65) Prior Publication Data

US 2023/0203128 A1 Jun. 29, 2023

Related U.S. Application Data

(63) Continuation of application No. 16/957,169, filed as application No. PCT/US2018/066979 on Dec. 20, 2018.

(60) Provisional application No. 62/611,957, filed on Dec. 29, 2017.

(51) Int. Cl.
| | |
|---|---|
| *C07K 14/705* | (2006.01) |
| *A61K 38/17* | (2006.01) |
| *A61K 39/00* | (2006.01) |
| *A61K 45/06* | (2006.01) |
| *A61P 35/00* | (2006.01) |

(52) U.S. Cl.
CPC ...... *C07K 14/70596* (2013.01); *A61K 38/177* (2013.01); *A61K 39/461* (2023.05); *A61K 39/4631* (2023.05); *A61K 39/464466* (2023.05); *A61K 45/06* (2013.01); *A61P 35/00* (2018.01); *C07K 2319/30* (2013.01)

(58) Field of Classification Search
CPC .......... C07K 14/70596; C07K 2319/30; A61K 38/177; A61P 35/00
See application file for complete search history.

(56) References Cited

U.S. PATENT DOCUMENTS

| | | | | |
|---|---|---|---|---|
| 8,889,628 | B2 * | 11/2014 | Shaw | A61P 9/10 424/134.1 |
| 9,631,018 | B2 | 4/2017 | Noelle | |
| 9,890,215 | B2 | 2/2018 | Noelle | |
| 10,858,436 | B2 | 12/2020 | Bradley | |
| 2013/0136741 | A1 | 5/2013 | Shaw | |

FOREIGN PATENT DOCUMENTS

| | | |
|---|---|---|
| WO | 2018132476 | 1/2018 |
| WO | 201816993 | 9/2018 |
| WO | 2019133454 | 7/2019 |

OTHER PUBLICATIONS

Liang, J-x, et al. (2016) Onco Targets Ther. 9:3113-3125. (doi: 10.2147/OTT.S102389).*
Zhang C, et al. (Jun. 2017) Am J Transplant. 17(6):1462-1475. (doi: 10.1111/ajt.14159).*
Matsumoto et al. (2009) Journal of Immunology 183:7204-7211; "P-Selectin Ligand-1 Negatively Regulates T-Cell Immune Responses".
Julien et al. (2007) Journal of Immunology 179:5701-5710; "Sialyl-Lewisx on P-Selectin Ligand-1 is Regulated During Differentiation and Maturation of Dendritic Cells: A Mechanism Involving the Glycotransferases C2GnT1 and ST3Gal I".
Nolo et al. (2017) Oncotarget 8:86657-86670; "Targeting P-Selectin Blocks Neuroblastoma Growth."
Kawecki et al. (2017) Journal of Thrombosis and Haemostasis 15:1285-1294; "Von Willebrand Factor and Inflammation".
Tsuchihashi et al. (2006) Journal of Immunology 176:616-624; "Molecular Characterization of Rat Leukocyte P-Selectin Glycoprotein Ligand-1 and Effect of Its Blockade: Protection from Ischemia-Reperfusion Injury in Liver Transplantation".
Veerman et al. (2007) Nature Immunology 8:532-539; "Interaction of the Selectin Ligand PSGL-1 with Chemokines CCL21 and CCL19 Facilitates Efficient Homing of T Cells to Secondary Lymphoid Organs".
Teachey et al. (2013) Blood 121:5154-5157) "Cytokine release syndrome after blinatumomab treatment related to abnormal macrophage activation and ameliorated with cytokine-directed therapy".
Ferber et al. (2017) eLife 2017:6:e25281 "Co-targeting the tumor endothelium and P-selectin-expressing glioblastoma cells leads to a remarkable therapeutic outcome".
Bonifant et al. (2016) Mol Ther Oncolytics, 3:16011; "Toxicity and management in CAR T-cell therapy".
Gray et al (2022) Front. Immunol.; 13:861670; "Negative Immune Checkpoint Protein, VISTA, Regulates the CD4+ Treg Population During Sepsis Progression to Promote Acute Sepsis Recovery and Survival".
El Tanbouly (2020) Clinical and Experimental Immunology, 200:120-130; "VISTA: Coming of age as a multi-lineage immune checkpoint".
Lines et al. (2014) Cancer Immunol Res; 2:510-517 "VISTA Is a Novel Broad-Spectrum Negative Checkpoint Regulator for Cancer Immunotherapy".
Hay et al. (2017) Blood 130: 2295-2306; "Kinetics and Biomarkers of Severe Cytokine Release Syndrome after CD19 Chimeric Antigen Receptor-modified T Cell Therapy".
Written Opinion of the International Searching Authority—PCT/US2018/066979 Aug. 16, 2019.
Gao et al. (2017) Nature Medicine 23:551-557 "VISTA is an inhibitory immune checkpoint that is increased after pilimumab therapy in patients with prostate cancer".
Deng et al. (2016) J. Immunotherapy of Cancer 4:86 "A New VISTA on combination therapy for negative checkpoint regulator blockade".
Mehta et al. (2020) Nature Scientific Reports 10:15171 "An engineered antibody binds a distinct epitope and is a potent inhibitor of murine and human VISTA".

(Continued)

*Primary Examiner* — Robert S Landsman

(57) ABSTRACT

Methods of using soluble tandem selectin glycoprotein ligand (TSGL) and TSGL fusion proteins, such as TSGL-Ig, in combination with T cell activation therapies or an adoptive cell transfer (ACT) therapy.

16 Claims, 5 Drawing Sheets

Specification includes a Sequence Listing.

(56) References Cited

OTHER PUBLICATIONS

Le Mercier et al. (2014) Cancer Research 74:1933-1944 "VISTA Regulates the Development of Protective Antitumor Immunity".
Johnston et al. (2019) Nature 574:565-570 "VISTA is an acidic pH-selective ligand for PSGL-1".
Kappelmayer and Nagy (2017) Biomed Research International 2017:Article ID 6138145 "The Interaction of Selectins and PSGL-1 as a Key Component in Thrombus Formation and Cancer Progression".
Muz et al. (2015) Biomed Research International 2015:Article ID 417586 "Inhibition of P-Selectin and PSGL-1 Using Humanized Monoclonal Antibodies Increases the Sensitivity of Multiple Myeloma Cells to Bortezomib".
Melero et al. (2020) J Immunother Cancer 8(supp 3):Abstract 315 "W0180 Novel Anti-VISTA Antibody: Rationale for Target Patient Population and First-in-Human Trial Design in Monotherapy and in Combination with Anti-PD1 Antibody".
Lines et al. (2020) J Immunother Cancer 8(supp 3):Abstract 447 "VISTA Targeting Remodels the Tumor Microenvironment to Overcome Adaptive Resistance".
Natoni et al. (2016) Frontiers in Oncology, 6:93 "Targeting Selectins and Their Ligands in Cancer."
Azab et al. (2012) Blood. 2012;119(6):1468-1478.

\* cited by examiner

```
                        *   *   *      sLex
                                        |
Fig 1a      Q A T E Y E Y L D Y D F L P E T/S E P P      [PSGL1-19]

*   *   *      sLex
                                |
Fig 1b      E Y E Y L D Y D F L P E T/S E P P            [PSGL4-19]

*   *          sLex
                                |
Fig 1c      E F E Y L D Y D F L P E T/S E P P            [PSGL4-19(Y5F)]

*      sLex
                                |
Fig 1d              D Y D F L P E T/S E P P              [PSGL9-19]
```

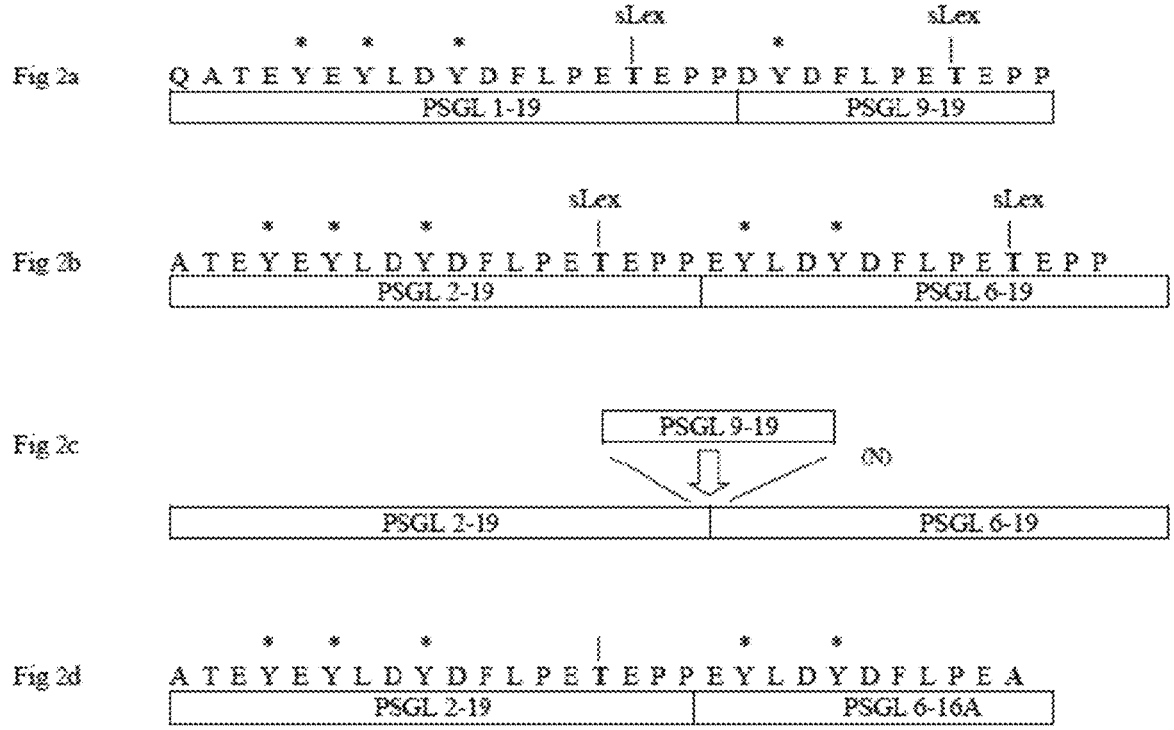

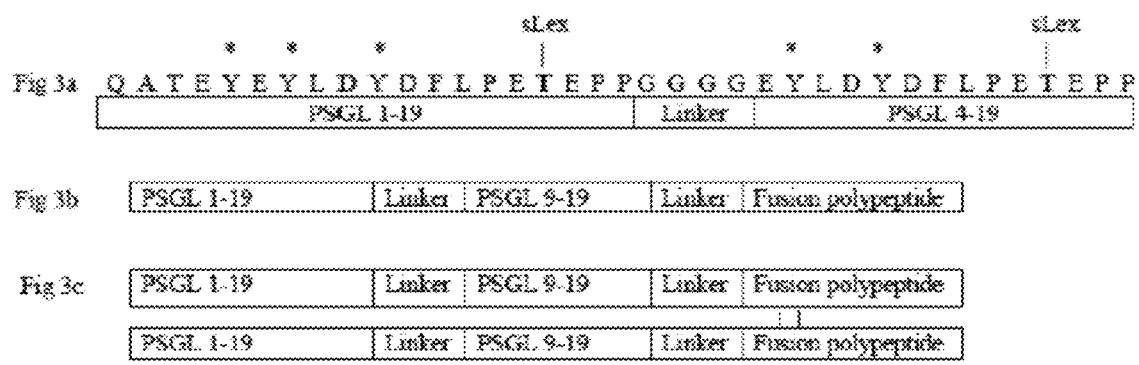

FIG. 5

Soluble TSGL molecule lacking sLe$^x$ fails to bind selectins yet retains binding activity to chemokines/other ligands

METHODS FOR TREATING CANCER USING SOLUBLE FORMS OF PSGL-1 AND FUSION MOLECULES THEREOF

RELATED APPLICATIONS

The present invention is a continuation of Ser. No. 16/957,169, filed Jun. 23, 2020, which was filed as a 371 national filing of International Patent Application Number PCT/US18/66979, filed on Dec. 21, 2018, which claimed priority from Provisional Patent Application 63/611,957, filed on Dec. 29, 2017.

SEQUENCE LISTING XML

The instant application contains a Sequence Listing which has been submitted electronically in XML format and is hereby incorporated by reference in its entirety. Said XML copy, created on Feb. 24, 2023, is named GDS-005-T1_SL.xml and is 9,514 bytes in size.

TECHNICAL FIELD

The present invention relates to the prevention, reduction and/or treatment of "off target" toxicities caused by therapies that activate T cells, including adoptive T cell therapies, while simultaneously enhancing their therapeutic activity. More particularly, the present invention is directed to novel uses of molecules comprising soluble binding domains from human P-selectin glycoprotein ligand (also known as "PSGL-1"), and molecules comprising two or more soluble binding PSGL-1 domains in tandem, known as tandem selectin glycoprotein ligand ("TSGL") molecules.

BACKGROUND OF THE INVENTION

Recently, several pioneering new T cell activating therapies have been developed to treat blood cell cancers and solid tumors. While many such therapies have exhibited promising efficacy, such therapies have also been noted to cause cytokine release syndrome (CRS), which in turn causes undesired adverse side effects in treated patients (Teachey et al. (2013) Blood 121:5154-5157). Elevated levels of circulating cytokines can promote unwanted vascular inflammation. In fact, activation of the vascular endothelium may increase capillary leak and permeability of the blood-brain barrier (BBB), leading to neurotoxicity (Gust et al. (2017) Cancer Discov, DOI: 10.1158/2159-8290.CD-17-0698). Damage to endothelial cells as a consequence of CRS has been measured by elevations in both the serum concentrations of von Willebrand Factor (VWF) and angiopoietin-2 (Ang-2 or ANGPT2) following CAR T cell infusions (Hay et al. (2017), Blood, doi.org/10.1182/blood-2017-06-793141) or following immune checkpoint modulation therapies (Wu et al. (2017) Cancer Immunol, DOI: 10.1158/2326-6066.CIR-16-0206). While agents such as tocilizumab, an anti-IL6 receptor antibody have demonstrated some usefulness in reducing the adverse effects of CRS, there is concern that agents such as tocilizumab may also reduce the therapeutic anti-cancer activity of the activated T cells (Bonifant et al. (2016) Mol Ther Oncolytics, 3:16011; doi:10.1038/mto. 2016.11; Hay et al. (2017)). Therefore, there is a need for agents and methods that can prevent the adverse events caused by CRS without compromising the anti-cancer activity of activated T cells.

The selectins (CD62P, CD62E, CD63L) are a family of C-type lectin cell adhesion molecules expressed, among other places, on certain types of circulating blood cells and on the activated vascular endothelium. During inflammation, leukocytes adhere to the vascular endothelium and enter subendothelial tissue, an interaction that is initially mediated by specific binding of the selectins to ligands on the surface of circulating cells. Such selectin-mediated cellular adhesion occurs during vascular inflammation, thrombotic disorders, parasitic diseases, and may be also implicated in metastatic spread of tumor cells. The selectin proteins are characterized by an N-terminal lectin-like domain, an epidermal growth factor-like domain, and regions of homology to complement binding proteins. Three human selectin proteins have been identified, E-selectin (formerly ELAM-1), L-selectin (formerly LAM-1) and P-selectin (formerly PADGEM or GMP-140). E-selectin is induced on endothelial cells several hours after activation by cytokines, mediating the calcium-dependent interaction between neutrophils and the endothelium. L-selectin is the lymphocyte homing receptor, and P-selectin rapidly appears on the cell surface of platelets when they are activated, mediating calcium-dependent adhesion of neutrophils or monocytes to platelets. P-selectin is also found in the Weibel-Palade bodies of endothelial cells; upon its release from these vesicles P-selectin mediates early binding of neutrophils to histamine- or thrombin-stimulated endothelium. All three of the selectins bind, with varying affinity, to a ligand called PSGL (P-selectin glycoprotein ligand and also known as "PSGL-1"). Interaction of selectins with PSGL, which is expressed on some circulating lymphocytes and leukocytes, causes those circulating cells in the vasculature which express the active form of PSGL to attach to platelets and/or the endothelium, where other adhesion molecules and chemokines then mediate extravasation into the surrounding tissues. Thus, the selectin/PSGL interaction has been a well-documented step in the development of inflammatory and immune responses, including vaso-occlusive crisis in sickle cell disease patients.

The cDNA encoding human PSGL (also termed PSGL-1 or SELPLG or CD162) has been cloned and is well-characterized as described in Larsen et al., WO98/08949, and U.S. Pat. No. 6,275,975, the disclosure and claims of which are hereby incorporated herein by reference. The application discloses polynucleotides encoding various forms of recombinant PSGL molecules, including numerous functional soluble forms of PSGL. Thus, PSGL is a well-characterized molecule, soluble forms of which are particularly amenable to administration as therapeutics to block selectin-mediated cell adhesion events (Busuttil et al. (2011) Am J Transplant, 11:786-97; Mertens et al. (2006) Am Heart J., 152:125 e1-e8).

The human form of PSGL contains over 300 amino acids in its extracellular domain (See, Uniprot database accession number Q14242). Remarkably, the principal binding site for P and L-selectin exists within a short 19 amino acid segment at the amino terminus of the mature form of PSGL. The highest reported affinity measurements of soluble monomeric forms of PSGL demonstrate $K_D$ values of approximately 200-778 nM when binding to P-selectin (Somers et al. (2000) Cell, 103:467-79; Leppanen et al. (1999) J. Biol. Chem., 274:24838-48). The binding affinity to E-selectin may vary according to the type and number of modified glycans present on the soluble form of PSGL. (Martinez et al. (2005) J. Biol. Chem 280:5378-5390). PSGL-1 interaction with selectins on their respective cell type, including soluble recombinant forms of PSGL-1, has been shown to induce signaling via the selectin molecules. The extent to which the selectin molecules are cross linked or clustered on the surface of a cell may dictate the characteristics of such selectin mediated signaling events generated in a particular cell type (Yoshida at el. (1998) *J Immunol;* 161:933-941). Moreover, it has been demonstrated that the chemokine CCL27 binds to the sulfated tyrosines at the amino terminus of human PSGL-1 (Hirata et al (2004) J. Biol. Chem. 279: 51775-51782).

Recent studies describe a role of PSGL in regulating T cell response in the tumor microenvironment and homing-independent functions of PSGL-1 in immune checkpoint regulation and T cell effector activity. (Tinoco et al. (2016) *Immunity;* 44:1190-1203; Barthel and Schatton (2016) *Immunity,* 44:1083-1085). FIG. 4D of WO2018132476 (Johnston et al.), indicates that full length human PSGL-1 molecules expressed on the surface of transfected CHO cells are capable of binding to multimers of the immune checkpoint molecule known as V-region Immunoglobulin-containing Suppressor of T cell Activation (VISTA) under acidic pH conditions (pH 6.0). The inventors interpreted their results to suggest that PSGL-1 may be a direct counter-receptor for VISTA under acidic conditions. The inventors theorized that PSGL-1 antagonists and/or VISTA antagonists may be useful in the treatment of cancer in combination with checkpoint inhibitors or other immuno-oncology agents. Additionally, Hmeljak et al. (2018) Cancer Discov; 8:1548-1565 discloses that VISTA is expressed on malignant pleural mesothelioma (MPM). It has also been reported that neuroblastoma tumors (Nolo et al. (2017) Oncotarget 8:86657-86670) and glioblastoma tumors (Ferber et al. (2017) eLife 2017:6:e25281) can be treated in vivo using molecules that specifically bind and target P-selectin.

U.S. Pat. No. 8,889,628 (Shaw) describes the production of enhanced soluble selectin ligands containing two or more sulfated glycoprotein peptide sequences from PSGL combined in a tandem configuration on a single peptide chain, designated as tandem selectin glycoprotein ligands, or TSGLs, and fusions of TSGLs with an immunoglobulin Fc, to form a TSGL fusion protein.

BRIEF SUMMARY OF THE INVENTION

The present invention describes methods of use of soluble forms of PSGL, such as a TSGL molecule or a TSGL fusion protein, for antitumor and anticancer therapies. The present invention further describes methods of using soluble forms of PSGL, such as TSGL molecules and TSGL fusion proteins, in combination with a therapy that involves activation of T cells, including cellular therapies such as cells genetically modified with a chimeric antigen receptor (CAR). Treatment with soluble forms of PSGL, such as TSGL molecules, help prevent the damage of endothelial cells following T cell activation, including reduction in the damage to the vascular endothelium caused, in part, by cytokine release syndrome (CRS).

U.S. Pat. No. 8,889,628 describes the production of soluble tandem selectin glycoprotein ligand (TSGL) molecules comprising at least two P-selectin glycoprotein ligand (PSGL) domains combined in a tandem configuration along the same polypeptide chain. The PSGL domains of such molecule preferably comprise at least one sulfated tyrosine and at least one O-linked glycan bearing a sialyl Lewis x (sLe$^x$) epitope. In certain aspects, one or more soluble PSGL domains may be missing the sLe$^x$ epitope, and therefore the TSGL molecules, may be partially lacking, or even be completely devoid of sLe$^x$ epitopes. The TSGL molecules may be fused to a non-TSGL polypeptide. Suitable non-TSGL polypeptides include, but are not limited to, an immunoglobulin Fc; SolCD39, a Kunitz domain polypeptide, a fibronectin type III domain, an XTEN polypeptide or MAP-1 (Skjoedt et al., *J. Biol. Chem.* 2010; 285: 8234-8243 and Pavlov et al., *Circulation* 2012; 126:2227-2235). In certain preferred embodiments, the TSGL molecule comprises an amino acid sequence having at least 70%, 80% or 90% sequence identity to the amino acid sequence of SEQ ID NO: 2. More preferably, the TSGL molecule comprises the amino acid sequence of SEQ ID NO: 2, or a functional variant thereof having at least 70% sequence identity to the amino acid sequence of SEQ ID NO: 2.

In certain aspects, the present invention provides methods of treatment of a subject having a tumor or a subject having cancer, said method comprising administering a soluble form of human PSGL-1 to said subject in combination with a cellular therapy, such as administration of cells genetically modified with a chimeric antigen receptor (CAR), for the treatment of tumors or cancer. The soluble form of PSGL-1 may comprise a soluble tandem selectin glycoprotein ligand (TSGL) molecule, or a TSGL fusion protein. In certain embodiments, each of the PSGL-1 domains of the TSGL molecule comprises amino acids 10 to 16 of SEQ ID NO:2 (YDFLPET). In certain embodiments, the method comprises administering a TSGL molecule or a TSGL fusion protein to said subject in combination with an adoptive cell transfer (ACT) therapy such as a cell genetically modified with a chimeric antigen receptor (CAR) for the treatment of tumors or cancer.

Without being bound to any particular theory of mechanism, it is contemplated that treatment of a subject with a molecule comprising at least one soluble PSGL-1 domain, such as a TSGL molecule or TSGL fusion protein, in combination, simultaneously with, or prior to ACT therapy, may prevent or lessen adverse immune effects of ACT, such as cytokine release syndrome (CRS), and/or other adverse effects of elevated cytokine levels. In certain embodiments, the molecule comprising at least one soluble PSGL-1 domain, such as a TSGL molecule or TSGL fusion protein, and/or ACT treatment may be administered in multiple doses or cycles. In certain embodiments, the subject may be treated with one or more additional medicaments intended to prevent or lessen adverse immune effects of ACT. Such additional medicaments may inhibit the release of one or more cytokines, or block the binding of a cytokine to its receptor. Such additional medicaments include, for example, an antagonist of a cytokine or cytokine receptor, such as tocilizumab, a monoclonal antibody that binds to IL-6 receptor and blocks the binding of IL-6 to its receptor.

It is further contemplated by the inventors herein, that the PSGL domains of a molecule comprising at least one soluble PSGL-1 domain, such as a TSGL molecule or TSGL fusion protein may be useful as a medicament for certain methods of treatment that are disclosed herein, for example, the molecule comprising at least one soluble PSGL-1 domain, such as a TSGL molecule or TSGL fusion protein, may be used in combination with an adoptive cell transfer (ACT) therapy, or other pro-immune therapy or agent; in methods of promoting immune activity, such as T-cell recruitment, activation or infiltration; and/or in methods of treating, preventing, lessening the incidence of, or lessening the severity of adverse effects of such ACT therapy or pro-immune therapy or agent, including treating or preventing cytokine release syndrome (CRS). Without being bound to any particular theory of mechanism, the inventor herein contemplates that the efficacy such molecules can be enhanced if one or more soluble PSGL domains of such molecules is missing one or more sLe$^x$ epitopes, and therefore the molecule comprising at least one soluble PSGL-1 domain, such as a TSGL molecule or TSGL fusion protein, may be partially lacking, or completely devoid of sLe$^x$ epitopes.

In other embodiments, treatment with a soluble form of human PSGL-1, such as a TSGL molecule or a TSGL fusion protein, is administered to a subject in combination with, simultaneously, or prior to, a therapy or agent intended to activate or promote immune activity, such as T-cell recruitment, activation or infiltration. For example, Gao et al. (2017) Nat. Med. 23:551-555, report that anti-CTLA-4 therapy may induce PD-L1 and VISTA molecules on subsets of macrophages within tumors. In the case of prostate tumors, increased VISTA expression appears to represent a compensatory inhibitor pathway that contributes to the tumor resistance of anti-CTLA-4 therapy. In such settings, a combination treatment with TSGL molecules may reduce the inhibition caused by VISTA. Pro-immune therapies include, for example, cancer vaccines, oncolytic viruses, gene therapy, and cellular therapies such as hematopoietic stem cell (HSC) and bone marrow transplantation Pro-immune agents include, for example, checkpoint inhibitors, and cytokines. Other pro-immune therapies and agents useful in the present invention include: blinatumomab, a CD19/CD3-bispecific single chain antibody that is designed to link CD19+ B cells with CD3+ T-cells, and induce a cytotoxic T-cell response against CD19+ B leukemia/lymphoma. Teachey et al. (2013) Blood 121:5154-5157. Another bispecific T-cell recruiting antibody is solitomab, a fusion protein consisting of two single-chain variable fragments (scFvs) binding to T cells via the CD3 receptor and to the EpCAM tumor associated antigen. (Amann et al. (2009) J. Immunotherapy 32:452-464.) A third bispecific, trifunctional antibody is catumaxomab (Removab®, Fresenius Biotech GmbH), a trifunctional antibody that binds to CD3/EpCAM and to Fc receptors via its intact Fc region. Seimetz (2011) J. Cancer 2:309-316.

The present invention further includes methods of treating or preventing cytokine release syndrome (CRS), comprising administering to a subject in need thereof a soluble form of human PSGL-1, such as a TSGL molecule or a TSGL fusion protein, in an amount effective to reduce the elevation of VWF or Ang-2 serum concentrations, wherein one or more of the soluble form of PSGL-1 domains in such TSGL molecule or TSGL fusion protein comprises amino acids 10 to 16 of SEQ ID NO:2 and wherein one or more of the soluble form of PSGL-1 domains in such molecule does not contain the sialyl Lewis X (sLe$^x$) tetrasaccharide. Accordingly, in certain embodiments, the molecule comprising at least one soluble PSGL-1 domain, such as a TSGL molecule or TSGL fusion protein, may be partially lacking, or completely devoid of sLe$^x$ epitopes.

In certain embodiments, the method comprises administering the soluble form of PSGL-1 domains, TSGL molecule or a TSGL fusion protein and ACT or other pro-immune therapy or agent in combination, simultaneously or nearly simultaneously. In other embodiments, the soluble form of PSGL-1 domains, TSGL molecule or TSGL fusion protein, may be administered after administration of ACT therapy, or other pro-immune therapy or agent. In other embodiments, the soluble form of PSGL-1 domains, TSGL molecule or TSGL fusion protein may be administered prior to administration of ACT therapy, or other pro-immune therapy or agent. In other aspects, the present invention comprises a method in which a soluble form of human PSGL-1, TSGL molecule or TSGL fusion protein, is administered to a subject prior to, or in combination with, an adoptive cell transfer (ACT) therapy, or other pro-immune therapy or agent, in order to treat, prevent, lessen the incidence of, or lessen the severity of adverse effects of such therapy or agent. The adverse effects may comprise cytokine release syndrome (CRS). The adverse effects may further comprise neurological effects, including seizures, headaches, delirium and edema. In certain embodiments, the soluble form of human PSGL-1, TSGL molecule or TSGL fusion protein may be administered at least 20 minutes, 30 minutes, 40 minutes, 50 minutes, 60 minutes, 70 minutes, 80 minutes, 90 minutes, 2 hours, 3 hours, 4 hours, 5 hours, 6 hours 7 hours, 8 hours, 10 hours, 12 hours, 14 hours, 16 hours, 18 hours, 20 hours, 22 hours, or 24 hours prior to use of an ACT. In certain other embodiments, the soluble form of human PSGL-1, TSGL molecule or TSGL fusion protein, may be administered at least 1 day, 2 days, 3 days, 4 days, 5 days, 6 days or 7 days prior to use of an ACT, or other pro-immune therapy or agent. In certain embodiments, multiple doses of the soluble form of human PSGL-1, TSGL molecule or TSGL fusion protein may be administered prior to beginning ACT treatment. In other embodiments, the soluble form of human PSGL-1, TSGL molecule or TSGL fusion protein and/or ACT treatment, or other pro-immune therapy or agent may be administered in multiple doses or cycles.

In certain embodiments, at least one additional active agent may be administered in combination with the ACT therapy and soluble form of human PSGL-1, TSGL molecule or TSGL fusion protein. In certain embodiments, the additional active agent is selected from the group consisting of immune checkpoint modulators. Immune checkpoint modulators useful in the present invention include both immune checkpoint inhibitors and immune checkpoint stimulators Immune checkpoint inhibitors useful in the present invention include PD-1 antagonists, PD-L1 antagonists, and CTLA-4 antagonists. In some embodiments, the immune checkpoint inhibitor is selected from the group consisting of nivolumab (Opdivo®, Bristol-Myers Squibb), ipilimumab (Yervoy®, Bristol-Myers Squibb); and pembrolizumab (Keytruda®, Merck). Other immune checkpoint inhibitors that are in development and may be used in the present invention include atezolizumab (Tecentriq®, Genentech/Roche), also known as MPDL3280A, a fully humanized engineered antibody of IgG1 isotype against PD-L1; durvalumab (Imfinzi®, Astra-Zeneca), also known as MEDI4736; tremelimumab (AstraZeneca), also known as CP-675,206, which is a fully human monoclonal antibody against CTLA-4; pidilizumab (CureTech), also known as CT-011, an antibody that binds to PD-1; avelumab (Bavencio®, Pfizer/Merck KGaA), also known as MSB0010718C), a fully human IgG1 anti-PD-L1 antibody; and PDR001 (Novartis), an inhibitory antibody that binds to PD-1. Immune checkpoint stimulators useful in the present invention include agonists of the following molecules: CD27, CD28, CD40, OX40 (CD134), GITR, ICOS and CD137 (4-1BB); for example, agonistic antibodies to ICOS (See Michaelson et al. (2016), Cancer Research Abstract #573, regarding Jounce antibody JTX-2011), agonistic antibodies to CD137 (e.g., Urelumab/BMS-663513/anti-4-1BB antibody), and agonistic antibodies to OX40, such as MEDI0562, MEDI 6469 and MEDI6383 (AstraZeneca), which are OX40 agonists and which can act as checkpoint stimulator molecules.

In other embodiments, the at least one additional active agent is selected from a protein kinase inhibitor or a VEGF-R antagonist. Protein kinase inhibitors or VEGF-R antagonists useful in the present invention include axitinib (Inlyta®, Pfizer Inc., NY, USA), sorafenib (Nexavar®, Bayer AG and Onyx); sunitinib (Sutent®, Pfizer, New York, US); pazopanib (Votrient®, GlaxoSmithKline, Research Triangle Park, US); cabozantinib (Cometriq®, Exelexis, US); regorafenib (Stivarga®, Bayer); lenvatinib (Lenvima®, Eisai); bevacizumab (Avastin®, Genentech, Inc. of South San Francisco, Calif.,), an anti-VEGF monoclonal antibody; and aflibercept, also known as VEGF Trap (Zaltrap®; Regeneron/Sanofi). Other kinase inhibitors/VEGF-R antagonists that are in development and may be used in the present invention include tivozanib (Aveo Pharmaceuticals, Cambridge, MA); vatalanib (Bayer, Novartis, Basel, Switzerland); lucitanib (Clovis Oncology); dovitinib (Novartis); CEP-11981 (Cephalon, US); linifanib (Abbott Laboratories, Abbott Park, US); PTC299 (PTC Therapeutics, South Plainfield, US); CP-547,632 (Pfizer); foretinib (Exelexis. GlaxoSmithKline); and motesanib (Amgen, Takeda).

The present invention also includes methods of use of soluble forms of human PSGL-1, TSGL molecules or TSGL fusion proteins for the treatment of viruses, including viruses that cause persistent and chronic viral infections. For example, the methods of the present invention are suitable for the treatment of HIV, hepatitis (A, B and C), Herpesviruses, lymphocytic choriomeningitis viruses (LCMV), human T-lymphotrophic virus (HTLV), respiratory syncytial virus (RSV), mumps virus, measles virus, rotaviruses, influenza viruses, enterovirus 71 land Flaviviruses, such as ZIKA, dengue, West Nile, Yellow Fever, and Japanese encephalitis viruses.

The present invention also includes methods of use of soluble forms of human PSGL-1, TSGL molecules or TSGL fusion proteins for the treatment of pathogenic bacterial infections, such as syphilis, *chlamydia*, rickettsial bacteria, mycobacteria, staphylococci, streptococci, pneumonococci, meningococci and conococci, *klebsiella, proteus, serratia, pseudomonas, legionella*, diphtheria, *salmonella*, bacilli, cholera, tetanus, botulism, anthrax, plague, leptospirosis, and Lymes disease bacteria, and diseases caused by pathogenic fungi or parasites, such as: *Candida* (*albicans, krusei, glabrata, tropicalis*, etc.), *Cryptococcus neoformans, Aspergillus* (*fumigatus, niger*, etc.), Genus *Mucorales* (*mucor, absidia*, rhizophus), *Sporothrix schenkii, Blastomyces dermatitidis, Paracoccidioides brasiliensis, Coccidioides immitis* and *Histoplasma capsulatum; Entamoeba histolytica, Balantidium coli*, Naegleriafowleri, *Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondii*, and *Nippostrongylus brasiliensis*; Escheria *coli, Clostridium dificil, Mycobacterium tuberculosis* and multidrug resistant organisms, including viruses and bacteria.

The present invention also includes methods of use of soluble forms of human PSGL-1, TSGL molecules or TSGL fusion proteins for the enhancement of activity of vaccines, for example, vaccines against viral infections, or other pathogenic infections. In certain embodiments, the soluble forms of human PSGL-1, TSGL molecules or TSGL fusion proteins may be administered in a single formulation with other elements of the vaccine. In other embodiments, the soluble forms of human PSGL-1, TSGL molecules or TSGL fusion proteins may be administered as a separate formulation, which may be co-administered with the vaccine. In other embodiments, the soluble forms of human PSGL-1, TSGL molecules or TSGL fusion proteins may be administered as a separate formulation prior to vaccination.

BRIEF DESCRIPTION OF THE FIGURES

FIG. 1 illustrates the protein structure of various monomeric sulfated PSGL-1 glycopeptide domains within the present invention. In each of the monomeric sulfated PSGL-1 glycopeptide domains, at least one tyrosine residue is sulfated, and the threonine, is the site of an O-linked glycan bearing a sialyl Lewis x (sLe$^x$) epitope (illustrated by the letters (T/S). FIG. 1a illustrates the sequence of the monomeric sulfated PSGL-1 glycopeptide domain [PSGL1-19] with tyrosine sulfation designated by asterisks, wherein the designation "[PSGL1-19]" means that the domain comprises amino acids 1 through 19 of the principal binding site for P and L-selectin found within human PSGL-1, illustrated at SEQ ID NO: 2. FIG. 1b illustrates the sequence of the monomeric sulfated PSGL-1 domain [PSGL4-19], which comprises amino acids 4 through 19 of SEQ ID NO:2. FIG. 1c illustrates the sequence of the monomeric sulfated PSGL-1 glycopeptide domain [PSGL4-19[Y5F]], which comprises amino acids 4 through 19 of SEQ ID NO:2, in which the tyrosine at amino acid residue 5 of the principal binding site for P and L-selectin found within human PSGL-1 [i.e., position 5 of SEQ ID NO: 2] has been converted to a phenylalanine FIG. 1d illustrates the sequence of the monomeric sulfated PSGL-1 glycopeptide domain [PSGL9-19], which comprises amino acids 9 through 19 of SEQ ID NO: 2,.

FIG. 2 illustrates the protein structure of the tandem configuration of sulfated PSGL-1 glycopeptide domains within the present invention [TSGLs]. FIG. 2a illustrates the structure of TSGL[PSGL1-19:PSGL9-19], wherein the designation "[PSGL1-19:PSGL9-19]" means that the TSGL comprises a first soluble PSGL-1 domain that comprises amino acids 1 through 19 of the principal binding site for P and L-selectin found within human PSGL-1; fused to a second soluble PSGL-1 domain that comprises amino acids 9 through 19 of the principal binding site for P and L-selectin found within human PSGL-1. FIG. 2b illustrates the structure of the TSGL [PSGL2-19:PSGL6-19]. FIG. 2c illustrates the structure of the TSGL [PSGL2-19:(PSGL9-19)N: PSGL6-19] within the present invention that contains more than two sulfated PSGL-1 glycopeptide domains, wherein N is one or greater and represents the number of sulfated PSGL9-19 glycopeptide domains between [PSGL2-19] and [PSGL6-19]. FIG. 2d illustrates the structure of the TSGL [PSGL2-19:PSGL6-16A], in which sLeX is not present and in which the threonine (T) residue at position 16 of the C-terminal PSGL unit has been substituted with an alanine (A) residue, signified by "16A".

FIG. 3 illustrates the protein structure and configuration of TSGL fusion proteins of the present invention with linker sequences between the two monomeric sulfated PSGL-1 glycopeptide domains of the TSGL and between the TSGL and the fusion polypeptide. FIG. 3a illustrates the amino acid sequence and structure of the TSGL [PSGL1-19 SEQ ID NO:2]:linker [amino acids 1 to 4 of SEQ ID NO:6]: PSGL6-19] [amino acids 6 to 19 of SEQ ID NO:2]. FIG. 3b illustrates the structure of the monomeric TSGL fusion protein [PSGL1-19:linker:PSGL9-19:linker:fusion polypeptide]. The fusion polypeptide may comprise, for example, an Fc region. FIG. 3c illustrates the structure of a multimeric TSGL fusion protein of the present invention. In this case two TSGL fusion proteins are linked via bonds between the two fusion polypeptides. For example, the fusion polypeptide region may each comprise an Fc region, and the two Fc regions may be linked to each other by means of a covalent disulfide bond.

In FIG. 4, each monomeric sulfated PSGL-1 glycopeptide domain presents a binding site for selectin, such that multiple selectins are able to bind to the TSGL fusion protein of the present invention.

FIG. 5 illustrates the structure and mechanism of enhanced binding of chemokines to a TSGL fusion protein of the present invention. In FIG. 5, each monomeric sulfated PSGL-1 glycopeptide domain lacks sLe$^x$, which ablates the ability to bind to selectins. However, the sulfated PSGL-1 domain retains the ability to bind to chemokines and other ligands or counter-receptors.

BRIEF DESCRIPTION OF THE SEQUENCES

Figure 4:
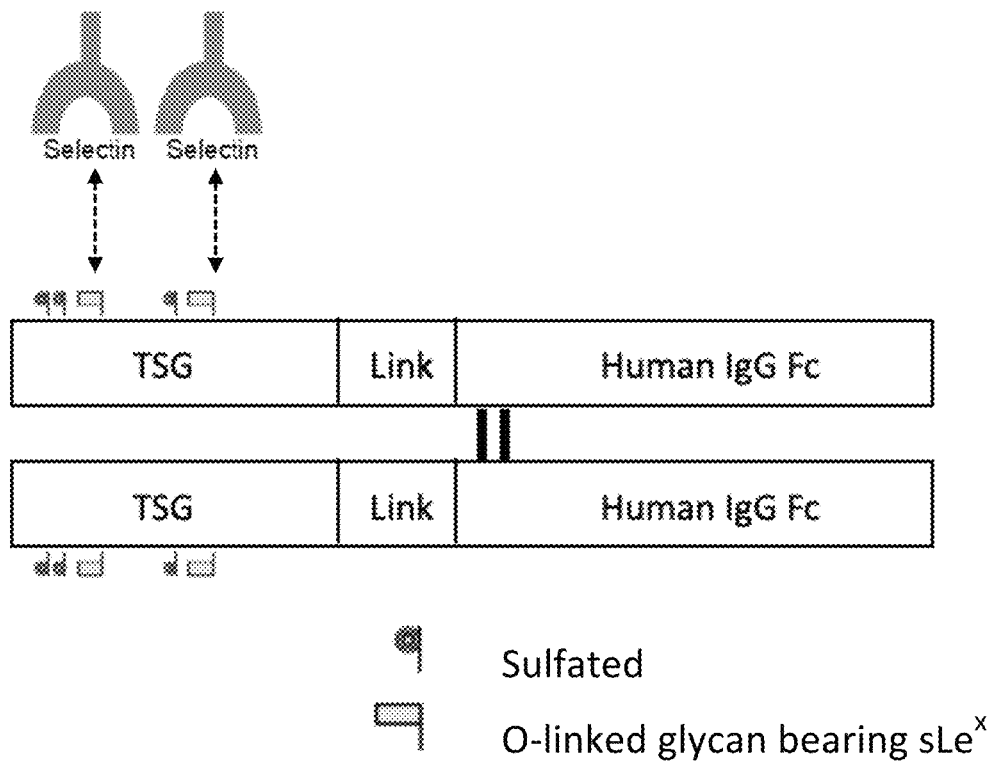
FIG. 4 illustrates the structure and mechanism of enhanced selectin binding exhibited by a TSGL fusion protein of the present invention.

SEQ ID NO: 1 is the amino acid sequence of human PSGL-1.

SEQ ID NO: 2 is the amino acid sequence of the principal binding site for P and L-selectin found within human PSGL-1.

SEQ ID NO: 3 is a nucleotide sequence encoding a tandem soluble glycoprotein ligand fusion protein, TSGL [PSGL1-19:PSGL5-19]-Fc, which is a TSGL fusion protein that is illustrative of the present invention.

SEQ ID NO: 4 is the protein sequence encoding a tandem soluble glycoprotein ligand fusion protein, TSGL[PSGL1-19:PSGL5-19]-Fc, which is a TSGL fusion protein that is illustrative of the present invention.

SEQ ID NO: 5 is the amino acid sequence of a glycine-serine linker sequence useful in the present invention.

SEQ ID NO: 6 is the amino acid sequence of a second glycine-serine linker sequence useful in the present invention.

SEQ ID NO: 7 is the amino acid sequence of a third glycine-serine linker sequence useful in the present invention.

DETAILED DESCRIPTION OF PREFERRED EMBODIMENTS

Human PSGL-1 is 412 amino acid protein (SEQ ID NO: 1) including a 17 amino acid N-terminal signal peptide (amino acids 1-17), a 24 amino acid N-terminal propeptide (amino acids 18-41) and a 371 amino acid P-selectin glycoprotein ligand 1 chain (amino acids 42-412).

```
SEQ ID NO: 1:
MPLQLLLLLI LLGPGNSLQL WDTWADEAEK ALGPLLARDR

RQATEYEYLD YDFLPETEPP EMLRNSTDTT PLTGPGTPES

TTVEPAARRS TGLDAGGAVT ELTTELANMG NLSTDSAAME

IQTTQPAATE AQTTQPVPTE AQTTPLAATE AQTTRLTATE

AQTTPLAATE AQTTPPAATE AQTTQPTGLE AQTTAPAAME

AQTTAPAAME AQTTPPAAME AQTTQTTAME AQTTAPEATE

AQTTQPTATE AQTTPLAAME ALSTEPSATE ALSMEPTTKR

GLFIPFSVSS VTHKGIPMAA SNLSVNYPVG APDHISVKQC

LLAILILALV ATIFFVCTVV LAVRLSRKGH MYPVRNYSPT

EMVCISSLLP DGGEGPSATA NGGLSKAKSP GLTPEPREDR

EGDDLTLHSF LP
```

The principal binding site for P and L-selectin is found within a 19 amino acid segment at the amino terminus of the mature form of PSGL from amino acids 42 to 60 (SEQ ID NO: 2). SEQ ID NO: QATEYEYLDY DFLPETEPP Soluble forms of PSGL-1 and TSGL molecules, including fusion proteins comprising enhanced TSGL sequences, can be expressed and purified from mammalian host cells, such as a Chinese hamster ovary cells (CHO) or COS cells. Suitable host cells contain tyrosylprotein sulfotransferase (TPST) enzymes (Moore et al., 106: 14741-14742, *Proc Natl Acad Sci* 2009) capable of modifying key PSGL-1 or TSGL tyrosine residues to form tyrosine O$^4$-sulfate esters. Suitable host cells are also capable of attaching carbohydrate side chains characteristic of functional soluble forms of human PSGL-1, TSGL molecules or TSGL fusion proteins. Such capability may arise by virtue of the presence of a suitable glycosylating enzyme within the host cell, whether naturally occurring, induced by chemical mutagenesis, or through transfection of the host cell with a suitable expression plasmid containing a DNA sequence encoding the glycosylating enzyme. These host cells can be transfected with expression vectors to enable, via posttranslational modification, the generation of the sialyl Lewis$^x$ epitope on the N-linked and O-linked glycans of enhanced PSGL polypeptides. In the case of CHO cells, this requires the co-expression of an α-1,3/1,4 fucosyltransferase (Kukowska-Latallo et al., Genes Dev. 4:1288-303, 1990) and Core2 β-1,6-N-acetylglucosaminyltransferase enzymes (Kumar et al., Blood 88:3872-79, 1996). The presence of the sialyl Lewis X epitopes on the N-linked and O-linked glycans of enhanced PSGL and/or immunoglobulin polypeptides may enhance the binding to selectins. In order to optimize processing of the mature N-terminus, these host cells may also be transfected with expression vectors with cDNA encoding a form of PACE, also known as furin, is disclosed in van den Ouweland et al., Nucl. Acids Res. 18, 664 (1990), the full disclosure of which is hereby incorporated herein by reference. Alternatively, soluble recombinant forms of human PSGL-1, TSGL molecules or TSGL fusion proteins without the sialyl Lewis x (sLe$^x$) epitope on its glycans may be produced in host cells such as CHO cells or HEK293 cells that lack appropriate modifying enzymes, such as the α-1,3/1,4 fucosyltransferase enzyme.

The principal binding site contains three tyrosines residues [at amino acids 5, 7 and 10 of SEQ ID NO: 2] for potential sulfation; and one threonine residue [at amino acid residue 16 of SEQ ID NO: 2] for an O-linked glycan bearing a sialyl Lewis x (sLe$^x$) epitope. Accordingly, in a preferred embodiment, each monomeric sulfated PSGL-1 glycopeptide domain contained within the soluble forms of human PSGL-1, TSGL molecules or TSGL fusion proteins of the present invention may comprise at least amino acids residues 10 to 16 of SEQ ID NO:2 (YDFLPET). In alternative embodiments, the monomeric sulfated PSGL-1 glycopeptide domain may each independently comprise one or more additional amino acids from the N-terminal end [e.g., amino acids 1-16; 2-16; 3-16; 4-16; 5-16; 6-16; 7-16; 8-16; or 9-16]; one or more additional amino acids from the C-terminal end [e.g., amino acids 10-17; 10-18; 10-19]; or one or more amino additional amino acids from both the N-terminal and C-terminal ends of SEQ ID NO: 2: [e.g. amino acids: 1-17; 2-17; 3-17; 4-17; 5-17; 6-17; 7-17; 8-17; and 9-17; 1-18; 2-18; 3-18; 4-18; 5-18; 6-18; 7-18; 8-18; and 9-18; or 1-19; 2-19; 3-19; 4-19; 5-19; 6-19; 7-19; 8-19; and 9-19]. In certain embodiments, the soluble forms of human PSGL-1, TSGL molecules or TSGL fusion proteins of the present invention comprise at least two sulfated PSGL-1 glycopeptide domains. In other embodiments, the soluble forms of human PSGL-1, TSGL molecules or TSGL fusion proteins of the present invention may comprise at least one additional monomeric sulfated PSGL-1 glycopeptide domain, that is, the soluble forms of human PSGL-1, TSGL molecules or TSGL fusion proteins comprises three or more sulfated PSGL-1 glycopeptide domains, with each PSGL-1 glycopeptide domain independently comprising at least amino acids 10 to 16 of SEQ ID NO: 2. Soluble forms of human PSGL-1, TSGL molecules or TSGL fusion proteins containing multiple sulfated residues increases the amount of negative (anionic) charge on the protein. Soluble forms of human PSGL-1, TSGL molecules or TSGL fusion proteins containing multiple sulfated residues can be purified from proteins having fewer sulfated residues (hyposulfated TSGL proteins) using methods similar to those described in U.S. Pat. No. 6,933,370.

A soluble form of human PSGL-1, or TSGL molecule of the present invention may be fused to amino acid sequences derived from one or more other proteins (e.g., a fragment of a protein that exhibits a desired activity), forming a soluble PSGL-1 fusion protein or a TSGL fusion protein, and the PSGL-1 fusion proteins or TSGL fusion proteins thereby formed constitute another aspect of the present invention. In any fusion protein incorporating a soluble PSGL-1 domain or TSGL protein, the amino acid sequence derived from one or more proteins other than P-selectin ligand can be linked to either the C-terminus or N-terminus of the enhanced PSGL-1 or TSGL sequence, or both. The linkage may be direct (i.e., without an intervening linking sequence not derived from either protein) or through a linking sequence. In certain embodiments of the invention, the soluble forms of human PSGL-1, TSGL molecules or TSGL fusion proteins are expressed from a recombinant DNA sequence which encodes both the soluble PSGL-1 domain or TSGL protein and the fusion polypeptide, joined either directly or via a DNA sequence encoding a linker sequence.

Suitable linker sequences are known in the art and include glycine-serine polymers (including, for example, (GS)n, (GSGGS)n [SEQ ID NO:5], (GGGGS)n [SEQ ID NO:6] and (GGGS)n [SEQ ID NO:7], where n is an integer of at least one, e.g., one, two, three, or four), glycine-alanine polymers, alanine-serine polymers, and other flexible linkers. Other examples include peptide linkers described in U.S. Pat. No. 5,073,627, the disclosure of which is hereby incorporated by reference.

Any protein or peptide that is desired to be targeted to cells expressing selectin molecules, for example, activated endothelial cells or activated platelets, can be fused with the TSGL in a TSGL fusion protein of the present invention. Proteins or polypeptides to which the TSGL proteins can be linked include, but are not limited to, SolCD39, Drosopoulos et al., Thromb. Haemost., 103:426-434 (2010), a Kunitz domain polypeptide (see, for example, Dennis and Lazarus, J. Biol. Chem., 269:22137-44 (1994); Nixon and Wood, Current Opinion in Drug Discovery and Development, 9:261-68 (2006)), a fibronectin type III domain (see for example, Dean et al., PNAS USA, 84:1876-80 (1987); Skorstengaard et al., Eur. J. Biochem., 161:441-53 (1986)), and XTEN polypeptides (Schellenberger et al, Nat. Biotechnol., 27:1186-90 (2009)). Other proteins or peptides which may be fused to a TSGL to form a TSGL fusion protein of the invention include, but are not limited to, cytokines, such as interleukin-1 receptor antagonist (IL-1Ra; Uniprot accession number P18510), bone morphogenetic proteins (BMPs; for example, BMP-2, Uniprot accession number P12643; BMP-4, Uniprot accession number P12644; BMP-7, Uniprot accession number P18075) and interleukin-11 (IL-11; Uniprot accession number P20809). In other embodiments, the protein or peptide which may be fused to a TSGL to form a TSGL fusion protein of the invention may be an enzyme, for example, including, but are not limited to, SolCD39 (Drosopoulos et al., Thromb. Haemost., 103:426-434 (2010)).

Adoptive Cellular Therapies (ACT)

Adoptive cellular therapies, or ACT, have been employed in a number of applications, primarily to increase the efficacy of the immune system to fight off disease such as a wide range of cancers. ACT may involve the enrichment, or expansion, of an immune cell population, such as autologous or allogeneic (donor) T-cells, natural killer (NK) cells, and/or hematopoietic stem cells (HSC), in order to provide larger doses of activated immune cells, such as tumor-infiltrating lymphocytes. See Besser et al. (2010) Clin. Cancer Res. 16:2646-2655. Other types of ACT involve genetic manipulation of immune cells, such as chimeric antigen receptor (CAR) therapy, in which cells are modified by the addition of chimeric antigen receptors in order to confer antigen recognition for tumor-associated antigens. CAR-modified T cells have been used in order to fight various forms of solid tumors, as well as CD19-expressing hematologic malignancies and other tumors and cancers. See Kalos et al. (2011) Science Translational Medicine 3:95ra73. At least two CAR-T therapies have been approved by the FDA, such as tisagenlecleucel (Kymriah®), and axicabtagene ciloleucel (Yescarta®), both CD-19-adopted CAR therapies used for B-cell acute lymphoblastic leukemia; and large B-cell lymphoma.

Both tisagenlecleucel and axicabtagene ciloleucel have black box warnings of the significant adverse side effects, primarily cytokine release syndrome or CRS, in which the immune system essentially kicks into overdrive and neurological problems including seizures, headaches, delirium and edema, and pose serious risks, including death. In order to prevent or lessen the risk of such adverse side effects, researchers have employed various approaches, including administration of tocilizumab, an IL-6 receptor antagonistic monoclonal antibody, to help block the binding of the cytokine IL-6 to its receptor. See Maude et al. (2014) Cancer J. 20:119-122; Bonifant et al. (2016) Molecular Therapy Oncolytics 3:16011.

TSGL Compositions and Formulations:

In certain embodiments, the composition comprising soluble PSGL-1 domains or TSGL further comprises one or more surfactants. Exemplary surfactants include, but are not limited to, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof. In certain embodiments, the surfactant is a Tween surfactant (e.g., Tween 60, Tween 80, etc.).

In certain embodiments, the composition further comprises one or more preservatives. Exemplary preservatives may include antioxidants, chelating agents, antimicrobial preservatives, antifungal preservatives, alcohol preservatives, acidic preservatives, and other preservatives.

In certain embodiments, the one or more preservative comprises an antioxidant. Exemplary antioxidants include, but are not limited to, phosphites, dibutyl phosphite, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, sodium sulfite, cysteine hydrochloride, thioglycerol, sodium mercaptoacetate, sodium formaldehyde sulfoxylate (SFS), lecithin, and alpha-tocopherol. In certain embodiments, the antioxidant is dibutyl phosphite or sodium bisulfite ($NaHSO_3$).

In certain embodiments, the one or more preservative comprises a chelating agent. Exemplary chelating agents include, but are not limited to, ethylenediaminetetraacetic acid (EDTA), citric acid monohydrate, disodium edetate, dipotassium edetate, edetic acid, fumaric acid, malic acid, phosphoric acid, sodium edetate, tartaric acid, and trisodium edetate.

In certain embodiments, the one or more preservative comprises an antimicrobial preservative. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

In certain embodiments, the one or more preservative comprises an antifungal preservative. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and sorbic acid.

In certain embodiments, the one or more preservative comprises an alcohol preservative. Exemplary alcohol preservatives include, but are not limited to, ethanol, polyethylene glycol, phenol, phenolic compounds, bisphenol, chlorobutanol, hydroxybenzoate, and phenylethyl alcohol.

In certain embodiments, the one or more preservative comprises an acidic preservative. Exemplary acidic preservatives include, but are not limited to, vitamin A, vitamin C, vitamin E, beta-carotene, citric acid, acetic acid, dehydroacetic acid, ascorbic acid, sorbic acid, and phytic acid.

Other preservatives include, but are not limited to, tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl.

In certain embodiments, the composition further comprises one or more diluents. Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and combinations thereof.

In certain embodiments, the composition further comprises one or more granulating and/or dispersing agents. Exemplary granulating and/or dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and combinations thereof.

In certain embodiments, the composition further comprises one or more binding agents. Exemplary binding agents include, but are not limited to, starch (e.g. cornstarch and starch paste); gelatin; sugars (e.g. sucrose, glucose, dextrose, dextrin, molasses, lactose, lactitol, mannitol, etc.); natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan); alginates; polyethylene oxide; polyethylene glycol; inorganic calcium salts; silicic acid; polymethacrylates; waxes; water; alcohol; etc.; and combinations thereof.

In certain embodiments, the composition further comprises one or more buffering agents. Exemplary buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and combinations thereof.

In certain embodiments, the composition further comprises one or more lubricating agents. Exemplary lubricating agents include, but are not limited to, magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

In certain embodiments, the composition further comprises one or more solubilizing or suspending agents. Exemplary solubilizing or suspending agents include, but are not limited to, water, organic solvents, oils, and mixtures thereof. Exemplary oils include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, *eucalyptus*, evening primrose, fish, flaxseed, geraniol, gourd, grape seed, hazel nut, hyssop, isopropyl myristate, jojoba, kukui nut, lavandin, lavender, lemon, *litsea* cubebs, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof. In certain embodiments, the oil is mineral oil.

Protein formulation is a well-known field and the skilled practitioner is readily able to design liquid formulations for administration via oral, injectable, intravenous, intrathecal, intramuscular and other routes, as well as stable lyophilized protein formulations, which may be administered orally, for example via capsule form, as well as other routes. See Carpenter et al. (1997) *Pharmaceutical Research*, 14:969-975; Manning et al. (2010) *Pharmaceutical Research*, 27:544-575; and Chang and Hershenson (2002) "Practical Approaches to Protein Formulation Development; in *Rational Design of Stable Protein Formulations*, Carpenter and Manning (eds), Volume 13 of the series *Pharmaceutical Biotechnology* (Springer U S).

In some embodiments, the pharmaceutically acceptable excipient is at least 95%, 96%, 97%, 98%, 99%, or 100% pure. In some embodiments, the excipient is approved for use in humans and for veterinary use. In some embodiments, the excipient is approved by United States Food and Drug Administration. In some embodiments, the excipient is pharmaceutical grade. In some embodiments, the excipient meets the standards of the United States Pharmacopoeia (USP), the European Pharmacopoeia (EP), the British Pharmacopoeia, and/or the International Pharmacopoeia.

The formulations of the pharmaceutical compositions described herein may be prepared by any method known or hereafter developed in the art of pharmacology. In general, such preparatory methods include the step of bringing the active ingredient or variant (e.g., a glycosylated variant) into association with a carrier and/or one or more other accessory ingredients, and then, if necessary and/or desirable, shaping and/or packaging the product into a desired single- or multi-dose unit.

A pharmaceutical composition of the invention may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

The relative amounts of the active ingredient, the pharmaceutically acceptable carrier, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) of the active ingredient.

Preferred dosage forms include oral and parenteral dosage forms. Liquid dosage forms for oral and parenteral administration include, but are not limited to, pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor, alcohols, oils, modified oils, glycols, polysorbates, cyclodextrins, polymers, and combinations thereof.

Injectable preparations, for example, sterile injectable aqueous or oleaginous suspensions may be formulated according to the known art using suitable dispersing or wetting agents and suspending agents. The sterile injectable preparation may be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are typically suppositories which can be prepared by mixing the conjugates of this invention with suitable non-irritating excipients or carriers such as cocoa butter, polyethylene glycol or a suppository wax which are solid at ambient temperature but liquid at body temperature and therefore melt in the rectum or vaginal cavity and release the active ingredient.

Compositions for oral administration are typically liquid or in solid dosage forms. Compositions for oral administration may include protease inhibitors, including organic acids such as citric acid, in order to inhibit pancreatic and brush border proteases. Compositions for oral administration may additionally include absorption enhancers, such as acylcarnitine and lauroylcarnitine, to facilitate the uptake of the peptide through the lumen of the intestine into the systemic circulation by a paracellular transport mechanism. Compositions for oral administration may additionally include detergents to improve the solubility of the peptides and excipients and to decrease interactions with intestinal mucus. Solid form compositions for oral administration, such as tablets or capsules, may typically comprise an enteric coating which further protects the peptides from stomach proteases and permits passage of the tablet or capsule into the small intestine. The solid form composition may additionally comprise a subcoat such as a non-ionic polymer. Examples of preparation of such orally available formulations are disclosed in U.S. Pat. Nos. 5,912,014, 6,086,918 and 6,673,574. The disclosure of each of these documents is hereby incorporated herein by reference.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid compositions of a similar type may be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type may be employed as fillers in soft and hard-filled gelatin capsules using such excipients as lactose or milk sugar as well as high molecular weight polethylene glycols and the like.

The active ingredients can be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient may be admixed with at least one inert diluent such as sucrose, lactose or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes.

A pharmaceutical composition of the invention may be prepared, packaged, and/or sold in a formulation suitable for pulmonary administration via the buccal cavity. Such a formulation may comprise dry particles which comprise the active ingredient and which have a diameter in the range from about 0.5 to about 7 nanometers or from about 1 to about 6 nanometers. Such compositions are conveniently in the form of dry powders for administration using a device comprising a dry powder reservoir to which a stream of propellant may be directed to disperse the powder and/or using a self-propelling solvent/powder dispensing container such as a device comprising the active ingredient dissolved and/or suspended in a low boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally, the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions of the invention formulated for pulmonary delivery may provide the active ingredient in the form of droplets of a solution and/or suspension. Such formulations may be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

The formulations described herein as being useful for pulmonary delivery are useful for intranasal delivery of a pharmaceutical composition of the invention. Another formulation suitable for intranasal administration is a coarse powder comprising the active ingredient and having an average particle from about 0.2 to 500 micrometers. Such a formulation is administered in the manner in which snuff is taken, i.e. by rapid inhalation through the nasal passage from a container of the powder held close to the nares.

Formulations suitable for nasal administration may, for example, comprise from about as little as 0.1% (w/w) and as much as 100% (w/w) of the active ingredient, and may comprise one or more of the additional ingredients described herein. A pharmaceutical composition of the invention may be prepared, packaged, and/or sold in a formulation suitable for buccal administration. Such formulations may, for example, be in the form of tablets and/or lozenges made using conventional methods, and may, for example, comprise 0.1 to 20% (w/w) active ingredient, the balance comprising an orally dissolvable and/or degradable composition and, optionally, one or more of the additional ingredients described herein. Alternately, formulations suitable for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition of the invention may be prepared, packaged, and/or sold in a formulation suitable for ophthalmic administration. Such formulations may, for example, be in the form of eye drops including, for example, a 0.1/1.0% (w/w) solution and/or suspension of the active ingredient in an aqueous or oily liquid carrier. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are contemplated as being within the scope of this invention.

General considerations in the formulation and/or manufacture of pharmaceutical agents may be found, for example, in *Remington: The Science and Practice of Pharmacy* 21$^{st}$ ed., Lippincott Williams & Wilkins, 2005.

The skilled clinician will be able to determine the appropriate dosage amount and number of doses of an agent to be administered to subject, dependent upon both the age and weight of the subject, the underlying condition, and the response of an individual patient to the treatment. In addition, the clinician will be able to determine the appropriate timing for delivery of the agent in a manner effective to treat the subject.

Preferably, the agent is delivered within 48 hours prior to exposure of the patient to an amount of a thrombosis or thrombocytopenia provoking stimulus effective to induce thrombosis or thrombocytopenia, and more preferably, within 36 hours, and more preferably within 24 hours, and more preferably within 12 hours, and more preferably within 6 hours, 5 hours, 4 hours, 3 hours, 2 hours, or 1 hour prior to exposure of the patient to an amount of thrombosis or thrombocytopenia provoking stimulus effective to induce thrombosis or thrombocytopenia. In one embodiment, the agent is administered as soon as it is recognized (i.e., immediately) by the subject or clinician that the subject has been exposed or is about to be exposed to a thrombosis or thrombocytopenia provoking stimulus, and especially a thrombosis or thrombocytopenia provoking stimulus to which the subject is sensitized. In another embodiment, the agent is administered upon the first sign of development of thrombosis or thrombocytopenia, and preferably, within at least 2 hours of the development of symptoms of thrombosis or thrombocytopenia, and more preferably, within at least 1 hour, and more preferably within at least 30 minutes, and more preferably within at least 10 minutes, and more preferably within at least 5 minutes of development of symptoms of thrombosis or thrombocytopenia. Symptoms of thrombosis or thrombocytopenia and methods for measuring or detecting such symptoms have been described and are well known in the art. Preferably, such administrations are given until signs of reduction of thrombosis or thrombocytopenia appear, and then as needed until the symptoms of thrombosis or thrombocytopenia are gone.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation.

Still further encompassed by the invention are kits that comprise one or more inventive complexes and/or compositions. Kits are typically provided in a suitable container (e.g., for example, a glass, foil, plastic, or cardboard package). In certain embodiments, an inventive kit may include one or more pharmaceutical excipients, pharmaceutical additives, therapeutically active agents, and the like, as described herein. In certain embodiments, an inventive kit may include means for proper administration, such as, for example, graduated cups, syringes, needles, cleaning aids, and the like. In certain embodiments, an inventive kit may include instructions for proper administration and/or preparation for proper administration.

Methods of Treatment:

The methods of the present invention may be useful in preventing undesired inflammation due, for example, to the production of cytokines, such as in cytokine release syndrome (CRS). The methods of the present invention may further be useful in aiding the anti-tumor or anticancer effects of therapies and treatments while preventing or reducing the occurrence of side effects, such as CRS and other forms of inflammation or destruction of normal tissue. Thus, the methods of the present invention include treatments of inflammatory disorders, as well as the moderation or prevention of side effects in pro-inflammatory and anti-cancer or anti-tumor treatments.

The compositions and kits of the present invention may be useful in treating conditions characterized by P-, E- or L-selectin mediated intercellular adhesion. Such conditions include, without limitation, myocardial infarction, bacterial or viral infection, metastatic conditions, inflammatory disorders such as arthritis, gout, uveitis, acute respiratory distress syndrome, asthma, emphysema, delayed type hypersensitivity reaction, systemic lupus erythematosus, thermal injury such as burns or frostbite, autoimmune thyroiditis, experimental allergic encephalomyelitis, multiple sclerosis, multiple organ injury syndrome secondary to trauma, diabetes, Reynaud's syndrome, neutrophilic dermatosis (Sweet's syndrome), inflammatory bowel disease, Grave's disease, glomerulonephritis, gingivitis, periodontitis, hemolytic uremic syndrome, ulcerative colitis, Crohn's disease, necrotizing enterocolitis, granulocyte transfusion associated syndrome, cytokine-induced toxicity, and the like.

The compositions and kits of the present invention may also be useful in organ transplantation, both to prepare organs for transplantation and to quell organ transplant rejection, as well as treating graft-vs-host disease. Accordingly, the compositions and kits of the present invention may be administered to a living or non-living organ donor, prior to organ removal, or may be administered "ex-vivo" to the donor organ concomitantly with organ preservation solution, prior to, and/or subsequent to surgical anastomosis with the recipient. The compositions and kits of the present invention may be used to treat hemodialysis and leukophoresis patients. Additionally, the compositions and kits of the present invention may be used as an antimetastatic agent, for example in the treatment of multiple myeloma. The compositions and kits of the present invention may be used itself as an inhibitor of P-, E- or L-selectin-mediated intercellular adhesion or to design inhibitors of selectin-mediated intercellular adhesion. The present invention encompasses both pharmaceutical compositions and kits of the present invention and therapeutic methods of treatment or use that employ the compositions and kits of the present invention.

Additional uses of the compositions and kits of the present invention include treatment of ischemia and reperfusion, bacterial sepsis and disseminated intravascular coagulation, adult respiratory distress syndrome and related pulmonary disorders, tumor metastasis, rheumatoid arthritis and atherosclerosis. Reperfusion injury is a major problem in clinical cardiology. Therapeutic agents that reduce leukocyte adherence in ischemic myocardium can significantly enhance the therapeutic efficacy of thrombolytic agents. Thrombolytic therapy with agents such as tissue plasminogen activator or streptokinase can relieve coronary artery obstruction in many patients with severe myocardial ischemia prior to irreversible myocardial cell death. However, many such patients still suffer myocardial neurosis despite restoration of blood flow. This "reperfusion injury" is known to be associated with adherence of leukocytes to vascular endothelium in the ischemic zone, presumably in part because of activation of platelets and endothelium by thrombin and cytokines that makes them adhesive for leukocytes (Romson et al., Circulation 67: 1016-1023, 1983). These adherent leukocytes can migrate through the endothelium and destroy ischemic myocardium just as it is being rescued by restoration of blood flow.

Bacterial sepsis and disseminated intravascular coagulation often exist concurrently in critically ill patients. They are associated with generation of thrombin, cytokines, and other inflammatory mediators, activation of platelets and endothelium, and adherence of leukocytes and aggregation of platelets throughout the vascular system. Leukocyte-dependent organ damage is an important feature of these conditions.

Adult respiratory distress syndrome is a devastating pulmonary disorder occurring in patients with sepsis or following trauma, which is associated with widespread adherence and aggregation of leukocytes in the pulmonary circulation. This leads to extravasation of large amounts of plasma into the lungs and destruction of lung tissue, both mediated in large part by leukocyte products. Two related pulmonary disorders that are often fatal are in immunosuppressed patients undergoing allogeneic bone marrow transplantation and in cancer patients suffering from complications that arise from generalized vascular leakage resulting from treatment with interleukin-2 treated LAK cells (lymphokine-activated lymphocytes). LAK cells are known to adhere to vascular walls and release products that are presumably toxic to endothelium. Although the mechanism by which LAK cells adhere to endothelium is not known, such cells could potentially release molecules that activate endothelium and then bind to endothelium by mechanisms similar to those operative in neutrophils.

Tumor cells from many malignancies (including carcinomas, lymphomas, and sarcomas) can metastasize to distant sites through the vasculature. The mechanisms for adhesion of tumor cells to endothelium and their subsequent migration are not well understood, but may be similar to those of leukocytes in at least some cases. Specifically, certain carcinoma cells have been demonstrated to bind to both E-selectin, as reported by Rice and Bevilacqua. Science 246: 1303-1306 (1991), and P-selectin, as reported by Aruffo, et al., Proc. Natl. Acad. Sci. USA 89:2292-2296 (1992). The association of platelets with metastasizing tumor cells has been well described, suggestion a role for platelets in the spread of some cancers. Since P-selectin is expressed on activated platelets, it is believed to be involved in association of platelets with at least some malignant tumors. Specific cancers where the methods of the present invention may be helpful include malignant pleural mesothelioma, neuroblastoma, and glioblastoma. Other cancers wherein the methods of the present invention may be useful include renal cell and kidney cancer, pancreatic cancer, lung cancer, liver cancer, bile duct cancer, breast cancer, ovarian cancer, testicular and prostate cancer, head and neck cancer, gastrointestinal and stomach cancer, endometrial cancer, bladder cancer, colon, rectal, colorectal, and anal cancer, thyroid cancer, non-melanoma skin cancer, melanoma, lymphoma and leukemia.

The compositions, materials and kits of the present invention may also be useful in methods of treating subjects having a tumor or cancer, and include methods using soluble forms of human PSGL-1, TSGL molecules or TSGL fusion proteins in combination with other antitumor and anticancer therapeutic molecules for enhanced antitumor and antitumor therapies, also termed immunotherapies. Soluble forms of human PSGL-1, TSGL molecules or TSGL fusion proteins may be combined with therapeutics known to modulate checkpoint molecules on T cells such as anti-PD-1 antibodies, anti-PD-L1 antibodies; anti-CTLA-4 antibodies, anti-ICOS antibodies, anti-CD137 antibodies, as well as other therapies and agents developed for such purposes. Such molecules may include, for example, inhibitors of adenosine A2A receptor; B7-H3 (CD276); B7-H4 (VTCN1); BTLA; CTLA-4; IDO; KIR; LAG3; PD-1; PD-L1; PD-L2; TIM-3; and VISTA.

The compositions, materials and kits of the present invention may also be useful in methods of treating subjects having pathogenic infections, whether viral, bacterial, fungal or parasitic in origin, and include methods using soluble forms of human PSGL-1, TSGL molecules or TSGL fusion proteins in combination with other antiviral, antibacterial, antifungal or anti-pathogenic and therapeutic molecules or treatments for enhanced anti-pathogenic therapies. In such indications, the soluble forms of human PSGL-1, TSGL molecules or TSGL fusion proteins may also be used in conjunction with therapeutics known to modulate checkpoint molecules. See, Velu et al. (2009) *Nature,* 458:7235; and Ha et al. (2008) *J. Experimental Medicine,* 205:543-555.

For the anti-cancer and anti-pathogenic uses of the present invention, the soluble forms of human PSGL-1, TSGL molecules or TSGL fusion proteins may not require $sLe^x$ be present. In these cases, the soluble forms of human PSGL-1, TSGL molecules or TSGL fusion proteins may, for example, be made in cells, such as CHO or HEK293, which lack the appropriate glycosylation enzymes, resulting in a soluble form of human PSGL-1, TSGL molecule or TSGL fusion protein that primarily binds via sulfated tyrosine residues.

Soluble forms of human PSGL-1, TSGL molecules or TSGL fusion proteins made in this manner would be expected to demonstrate antagonistic effects needed to inhibit PD-1 activity of T cells, but would likely not block selectin mediated trafficking of T cells, or that of neutrophils and monocytes. See Veerman et al. 2012, *J. Immunology*, 188: 1638-1646; Ley and Kansas 2004, *Nature Reviews*, 4:1-11. The present inventors theorize that soluble forms of human PSGL-1, TSGL molecules or TSGL fusion proteins, whether partially or fully lacking the sLe$^x$ epitope, yet retaining sulfated tyrosines, may be especially useful in anti-cancer and anti-pathogenic uses, since they will presumably stimulate T cells in the tumor or pathogen microenvironment, without adversely affecting the normal interaction between PSGL-1 and selectin molecules.

Additionally, the soluble forms of human PSGL-1, TSGL molecules or TSGL fusion proteins of the invention may be used in vaccines in order to promote, or enhance, immunity, such as to pathogenic viruses, bacteria, fungi and parasites. The soluble forms of human PSGL-1, TSGL molecules or TSGL fusion proteins may be administered, along with other immune-boosting and/or antigenic treatments in order to enhance immune responses to pathogenic infections. See, Velu et al., and Ha et al.

Platelet-leukocyte interactions are believed to be important in atherosclerosis. Platelets might have a role in recruitment of monocytes into atherosclerotic plaques; the accumulation of monocytes is known to be one of the earliest detectable events during atherogenesis. Rupture of a fully developed plaque may not only lead to platelet deposition and activation and the promotion of thrombus formation, but also the early recruitment of neutrophils to an area of ischemia.

Another area of potential application is in the treatment of rheumatoid arthritis. In these clinical applications, the glycoprotein ligand, or fragments thereof, can be administered to block selectin-dependent interactions by binding competitively to P-selectin expressed on activated cells. In particular, carbohydrate components of the ligand, which play a key role in recognition by P-selectin, can be administered. Similarly, natural or synthetic analogs of the ligand or its fragments which bind to P-selectin can also be administered. In addition, antibodies to the protein and/or carbohydrate components of the ligand, or fragments thereof, can be administered. The antibodies are preferably of human origin or modified to delete those portions most likely to cause an immunogenic reaction. Carbohydrate components of the ligand or the antibodies, in an appropriate pharmaceutical carrier, are preferably administered intravenously where immediate relief is required. The carbohydrate(s) can also be administered intramuscularly, intraperitoneally, subcutaneously, orally, as the carbohydrate, conjugated to a carrier molecule, or in a drug delivery device. The carbohydrate can be modified chemically to increase its in vivo half-life. See U.S. Pat. Nos. 6,506,382 and 8,232,252, the complete disclosures of which are hereby incorporated herein by reference.

Practice of the invention is illustrated in the following, non-limiting examples. The skilled artisan, having read the present specification, will recognize that many modifications, variations and extensions are possible without deviating from the teachings of the present specification. Those modifications, variations and extensions form a part of the invention, and will be recognized to constitute subject matter that may be embodied within the claims.

Example 1

TSGL Fusion proteins. A TSGL with a novel amino acid sequence can be constructed in accordance with the following procedure:

TSGL[PSGL1-19:PSGL6-19]-Fc: A cDNA was constructed encoding the signal peptide, PACE cleavage site and a 33 amino acid sulfated TSGL sequence fused to a mutated Fc region of human IgG1 at His224 (Kabat et al.) of the native Fc sequence. O-linked glycans bearing the sialyl Lewis x (sLe$^x$) epitope occur at the Thr16 and Thr30 residues of the mature protein in the case where the host cell is engineered to expresses an appropriate modifying enzymes such as α-1,3/1,4 fucosyltranseferase. The version of this TSGL molecule without sLe$^x$-modified glycans is produced in host cells that lack the glycan modifying enzymes.

The sequence of the cDNA construct is reported as SEQ ID NO:3. The amino acid sequence encoded by the cDNA construct is reported as SEQ ID NO:4. The mature amino acid sequence of the encoded fusion protein begins at amino acid 42 of SEQ ID NO:4. The mutations in the Fc portion were a change of Leu 234 and Gly237 of the native Fc sequence to Ala.

SEQ ID NO: 3

```
atgcctctgcaactcctcctgttgctgatcctactgggccctggcaacagcttgcagctg    60
tgggacacctgggcagatgaagccgagaaagccttgggtccctgcttgcccgggaccgg
agacaggccaccgaatatgagtacctagattatgatttcctgccagaaacggagcctcca   180
gagtacctagattatgatttcctgccagaaacggagcctccacacacatgcccaccgtgc
ccagcacctgaagccctgggggcaccgtcagtcttcctcttccccccaaaacccaaggac   300
accctcatgatctcccggacccctgaggtcacatgcgtggtggtggacgtgagccacgaa
gaccctgaggtcaagttcaactggtacgtggacggcgtggaggtgcataatgccaagaca   420
aagccgcgggaggagcagtacaacagcacgtaccgtgtggtcagcgtcctcaccgtcctg
caccaggactggctgaatggcaaggagtacaagtgcaaggtctccaacaaagccctccca   540
gcccccatcgagaaaaccatctccaaagccaaagggcagccccgagaaccacaggtgtac
accctgcccccatcccgggatgagctgaccaagaaccaggtcagcctgacctgcctggtc   660
aaaggcttctatcccagcgacatcgccgtggagtgggagagcaatgggcagccggagaac
aactacaagaccacgcctcccgtgctggactccgacggctccttcttcctctacagcaag   780
ctcaccgtggacaagagcaggtggcagcaggggaacgtcttctcatgctccgtgatgcat
gaggctctgcacaaccactacacgcagaagagcctctccctgtctccgggtaaatga      897
```

SEQ ID NO: 4

```
MPLQLLLLLI LLGPGNSLQL WDTWADEAEK ALGPLLARDR RQATEYEYLD YDFLPETEPP
EYLDYDFLPE TEPPHTCPPC PAPEALGAPS VFLFPPKPKD TLMISRTPEV TCVVVDVSHE
DPEVKFNWYV DGVEVHNAKT KPREEQYNST YRVVSVLTVL HQDWLNGKEY KCKVSNKALP
APIEKTISKA KGQPREPQVY TLPPSRDELT KNQVSLTCLV KGFYPSDIAV EWESNGQPEN
NYKTTPPVLD SDGSFFLYSK LTVDKSRWQQ GNVFSCSVMH EALHNHYTQK SLSLSPGK
```

Testing of the efficacy of the soluble forms of human PSGL-1, TSGL molecules or TSGL fusion proteins in anti-tumor and anticancer indications can be accomplished, for example, using methods such as those described in U.S. Pat. No. 9,073,994, for cytotoxicity, effects on tumor growth and proliferation, survival rates, interferon production, PDL-1 and PDL-2 expression, ICAM-1 expression, and other relevant assays. Testing the efficacy of soluble forms of human PSGL-1, TSGL molecules or TSGL fusion proteins to reduce cytokine release syndrome and neurotoxicity can be accomplished using preclinical xenograft models such as described by Sterner R M et al. (2018) Blood: blood-2018-10-881722.

All patents, patent applications and scientific literature references cited in the disclosure are hereby incorporated herein by reference for the cited teachings, as if fully set forth in the specification.

```
SEQUENCE LISTING

Sequence total quantity: 7
SEQ ID NO: 1            moltype = AA   length = 412
FEATURE                 Location/Qualifiers
source                  1..412
                        mol_type = protein
                        organism = Homo sapiens
SEQUENCE: 1
MPLQLLLLLI LLGPGNSLQL WDTWADEAEK ALGPLLARDR RQATEYEYLD YDFLPETEPP  60
EMLRNSTDTT PLTGPGTPES TTVEPAARRS TGLDAGGAVT ELTTELANMG NLSTDSAAME  120
IQTTQPAATE AQTTQPVPTE AQTTPLAATE AQTTRLTATE AQTTPLAATE AQTTPPAATE  180
AQTTQPTGLE AQTTAPAAME AQTTAPAAME AQTTPPAAME AQTTQTTAME AQTTAPEATE  240
AQTTQPTATE AQTTPLAAME ALSTDPSATE ALSMDPTTKR GLFIPFSVSS VTHKGIPMAA  300
SQLSVQYPVG APDHISVKQC LLAILILALV ATIFFVCTVV LAVRLSRKEH MKPVRNKSPT  360
EMVCISSLLP DGGEGPSATA NGGLSKAKSP GLTPEPREDR EGDDLTLHSF LP          412

SEQ ID NO: 2            moltype = AA   length = 19
FEATURE                 Location/Qualifiers
source                  1..19
                        mol_type = protein
                        organism = Homo sapiens
SEQUENCE: 2
QATEYEYLDY DFLPETEPP                                               19

SEQ ID NO: 3            moltype = DNA  length = 897
FEATURE                 Location/Qualifiers
source                  1..897
                        mol_type = other DNA
                        organism = synthetic construct
                        note = Synthesized
SEQUENCE: 3
atgcctctgc aactcctcct gttgctgatc ctactgggcc ctggcaacag cttgcagctg   60
tgggacacct gggcagatga agccgagaaa gccttgggtc cctgcttgc ccgggaccgg  120
agacaggcca ccgaatatga gtacctagat tatgatttcc tgccagaaac ggagcctcca  180
gagtacctag attatgattt cctgccagaa acggagcctc cacacacatg cccaccgtgc  240
ccagcacctg aagccctggg ggcaccgtca gtcttcctct tccccccaaa acccaaggac  300
accctcatga tctcccggac ccctgaggtc acatgcgtgg tggtggacgt gagccacgaa  360
gaccctgagg tcaagttcaa ctggtacgtg gacggcgtgg aggtgcataa tgccaagaca  420
aagccgcggg aggagcagta caacagcacg taccgtgtgg tcagcgtcct caccgtcctg  480
caccaggact ggctgaatgg caaggagtac aagtgcaagg tctccaacaa agccctccca  540
gcccccatcg agaaaaccat ctccaaagcc aaagggcagc cccgagaacc acaggtgtac  600
accctgcccc catcccggga tgagctgacc aagaaccagg tcagcctgac ctgcctggtc  660
aaaggcttct atcccagcga catcgccgtg gagtgggaga gcaatgggca gccggagaac  720
aactacaaga ccacgcctcc cgtgctggac tccgacggct ccttcttcct ctacagcaag  780
ctcaccgtgg acaagagcag gtggcagcag gggaacgtct tctcatgctc cgtgatgcat  840
gaggctctgc acaaccacta cacgcagaag agcctctccc tgtctccggg taaatga     897

SEQ ID NO: 4            moltype = AA   length = 298
FEATURE                 Location/Qualifiers
source                  1..298
                        mol_type = protein
                        organism = synthetic construct
                        note = Synthesized
SEQUENCE: 4
MPLQLLLLLI LLGPGQSLQL WDTWADEAEK ALGPLLARDR RQATEYEYLD YDFLPETEPP   60
EYLDYDFLPE TEPPHTCPPC PAPDALGAPS VFLFPPKPKD TLMISRTPEV TCVVVDVSHE  120
DPEVKFNWYV DGVEVHNAKT KPREEQKNST YRVVSVLTVL HQDWLNGKEY KCKVSNKALP  180
APIEKTISKA KGQPREPQVK TLPPSRDELT KNQVSLTCLV KGFYPSDIAV EWESNGQPEN  240
NYKTTPPVLD SDGSFFLYSK LTVDKSRWQQ GNVFSCSVMH DALHNHYTQK SLSLSPGK    298

SEQ ID NO: 5            moltype = AA   length = 5
FEATURE                 Location/Qualifiers
source                  1..5
                        mol_type = protein
                        organism = synthetic construct
                        note = Synthesized
SEQUENCE: 5
```

-continued

| | |
|---|---|
| GSGGS | 5 |

```
SEQ ID NO: 6          moltype = AA   length = 5
FEATURE               Location/Qualifiers
source                1..5
                      mol_type = protein
                      organism = synthetic construct
                      note = Synthesized
SEQUENCE: 6
```

| | |
|---|---|
| GGGGS | 5 |

```
SEQ ID NO: 7          moltype = AA   length = 4
FEATURE               Location/Qualifiers
source                1..4
                      mol_type = protein
                      organism = synthetic construct
                      note = Synthesized
SEQUENCE: 7
```

| | |
|---|---|
| GGGS | 4 |

What is claimed is:

1. A method of treating a cancer, comprising administering to a subject in need thereof a soluble form of human PSGL-1 in an amount effective to treat the cancer, wherein the soluble form of PSGL-1 comprises a soluble tandem selectin glycoprotein ligand (TSGL) comprising greater than one PSGL-1 domain, wherein each of the greater than one PSGL-1 domains comprises amino acids 5 to 16 of SEQ ID NO:2, and wherein the TSGL molecule is fused to a non-TSGL polypeptide and the TSGL molecule does not contain sialyl Lewis X (sLex) tetrasaccharide.

2. The method of treating a cancer according to claim 1, wherein the TSGL molecule is fused to a non-TSGL polypeptide; wherein the non-TSGL polypeptide fusion polypeptide is an immunoglobulin Fc and the TSGL molecule does not contain sialyl Lewis X (sLeX) tetrasaccharide.

3. The method of treating a cancer according to claim 1, wherein the cancer is selected from the group consisting of malignant pleural mesothelioma neuroblastoma or glioblastoma.

4. The method of treating a cancer according to claim 1, wherein the cancer is selected from the group consisting of multiple myeloma, renal cell and kidney cancer, pancreatic cancer, lung cancer, liver cancer, bile duct cancer, breast cancer, ovarian cancer, testicular and prostate cancer, head and neck cancer, gastrointestinal and stomach cancer, endometrial cancer, bladder cancer, colon, rectal, colorectal, and anal cancer, thyroid cancer, non-melanoma skin cancer, melanoma, lymphoma and leukemia.

5. The method of treating a cancer according to claim 2, wherein the cancer is selected from the group consisting of malignant pleural mesothelioma neuroblastoma or glioblastoma.

6. The method of treating a cancer according to claim 2, wherein the cancer is selected from the group consisting of multiple myeloma, renal cell and kidney cancer, pancreatic cancer, lung cancer, liver cancer, bile duct cancer, breast cancer, ovarian cancer, testicular and prostate cancer, head and neck cancer, gastrointestinal and stomach cancer, endometrial cancer, bladder cancer, colon, rectal, colorectal, and anal cancer, thyroid cancer, non-melanoma skin cancer, melanoma, lymphoma and leukemia.

7. The method of claim 1, further comprising administering at least one other active agent selected from the group consisting of a checkpoint modulator and a protein kinase inhibitor.

8. The method of claim 2, further comprising administering at least one other active agent selected from the group consisting of a checkpoint modulator and a protein kinase inhibitor.

9. The method of claim 1, in which one or more threonine (T) residues within the greater than one PSGL-1 domains comprising amino acids 5 to 16 of SEQ ID NO:2 have been replaced by an alanine (A) residue.

10. A method of treating a cancer, comprising administering to a subject in need thereof a soluble form of human PSGL-1 in an amount effective to treat the cancer, wherein the soluble form of PSGL-1 comprises a soluble tandem selectin glycoprotein ligand (TSGL) comprising greater than one PSGL-1 domain, wherein each of the greater than one PSGL-1 domains comprises amino acids 10 to 16 of SEQ ID NO2, and wherein the TSGL molecule is fused to a non-TSGL polypeptide and the TSGL molecule does not contain sialyl Lewis X (sLex) tetrasaccharide.

11. The method of treating a cancer according to claim 10, wherein the TSGL molecule is fused to a non-TSGL polypeptide; wherein the non-TSGL polypeptide fusion polypeptide is an immunoglobulin Fc and the TSGL molecule does not contain sialyl Lewis X (sLex) tetrasaccharide.

12. The method of treating a cancer according to claim 10, wherein the cancer is selected from the group consisting of malignant pleural mesothelioma neuroblastoma or glioblastoma.

13. The method of treating a cancer according to claim 11, wherein the cancer is selected from the group consisting of multiple myeloma, renal cell and kidney cancer, pancreatic cancer, lung cancer, liver cancer, bile duct cancer, breast cancer, ovarian cancer, testicular and prostate cancer, head and neck cancer, gastrointestinal and stomach cancer, endometrial cancer, bladder cancer, colon, rectal, colorectal, and anal cancer, thyroid cancer, non-melanoma skin cancer, melanoma, lymphoma and leukemia.

14. The method of treating a cancer according to claim 10, wherein the cancer is selected from the group consisting of malignant pleural mesothelioma neuroblastoma or glioblastoma.

15. The method of treating a cancer according to claim 11, wherein the cancer is selected from the group consisting of multiple myeloma, renal cell and kidney cancer, pancreatic cancer, lung cancer, liver cancer, bile duct cancer, breast cancer, ovarian cancer, testicular and prostate cancer, head and neck cancer, gastrointestinal and stomach cancer, endometrial cancer, bladder cancer, colon, rectal, colorectal, and anal cancer, thyroid cancer, non-melanoma skin cancer, melanoma, lymphoma and leukemia.

16. The method of claim 10, in which one or more threonine (T) residues within the greater than one PSGL-1 domains comprising amino acids 10 to 16 of SEQ ID NO:2 have been replaced by an alanine (A).

* * * * *